United States Patent [19]

Tsao

[11] Patent Number: 4,889,689

[45] Date of Patent: Dec. 26, 1989

[54] METHOD OF DISINFECTING A SOFT CONTACT LENS WITH A DIETHYLENE TRIAMINE PENTA(METHYLENEPHOSPHONIC ACID) STABILIZED HYDROGEN PEROXIDE SOLUTION

[75] Inventor: Fupao Tsao, Lawrenceville, Ga.

[73] Assignee: Ciba-Geigy Corporation, Ardsley, N.Y.

[21] Appl. No.: 264,597

[22] Filed: Oct. 31, 1988

Related U.S. Application Data

[63] Continuation of Ser. No. 917,947, Oct. 14, 1986, abandoned.

[51] Int. Cl.$^4$ ............................ A61L 9/00; A61K 33/40
[52] U.S. Cl. ........................................ 422/30; 252/106; 252/186.28; 252/186.29; 252/186.43; 422/28; 423/272; 423/273; 424/616; 514/715; 514/840
[58] Field of Search ................. 252/95, 100, 102, 106, 252/186.28, 186.29, 186.43; 423/272, 273; 422/28, 30; 424/130; 514/714, 839, 840

[56] References Cited

U.S. PATENT DOCUMENTS

| | | | |
|---|---|---|---|
| 3,114,606 | 12/1963 | Meeker | 423/273 |
| 3,122,417 | 2/1964 | Blaser et al. | 23/207.5 |
| 3,234,140 | 2/1966 | Irani | 252/186.29 |
| 3,333,925 | 8/1967 | Reilly | 423/273 |
| 3,356,457 | 12/1967 | Morris et al. | 423/273 |
| 3,387,939 | 6/1968 | Reilly et al. | 423/273 |
| 3,429,666 | 2/1969 | Morris et al. | 423/273 |
| 3,591,341 | 7/1971 | Reilly | 423/273 |
| 3,607,053 | 9/1971 | Reilly | 423/273 |
| 3,687,627 | 8/1972 | Stalter | 423/271 |
| 3,860,391 | 1/1975 | Kling et al. | 8/111 |
| 4,294,575 | 10/1981 | Kowalski | 8/111 |
| 4,304,762 | 12/1981 | Leigh | 423/272 |
| 4,347,149 | 8/1982 | Smith et al. | |
| 4,362,706 | 12/1982 | Willard | 423/273 |
| 4,414,127 | 11/1983 | Fu | 252/95 |
| 4,521,375 | 6/1985 | Houlsby | 422/29 |
| 4,525,291 | 6/1985 | Smith et al. | 252/95 |
| 4,585,488 | 4/1986 | Giefer | 134/27 |
| 4,599,195 | 7/1986 | Schäfer et al. | 252/546 |
| 4,614,646 | 9/1986 | Christiansen | 423/272 |

FOREIGN PATENT DOCUMENTS

1500707 2/1978 United Kingdom .

OTHER PUBLICATIONS

Dequest 2000 and 2006 Product Literature, p. 5.
Dequest 2010, Product Literature, p. 2.
Dequest 2060 Product Literature, Tech. Bulletin No. IC/SCS-323, pp. 3–25.
Janoff, Lester, E., "The Effective Disinfection of Soft Contact Lenses Using Hydrogen Peroxide", *The Optician*, Aug. 3, 1979, pp. 24, 29, 30.

*Primary Examiner*—Prince E. Willis
*Attorney, Agent, or Firm*—Irving M. Fishman

[57] ABSTRACT

A method of disinfecting a soft contact lens with a stabilized aqueous hydrogen peroxide solution having a pH between about 5.5 and about 7.5, a hydrogen peroxide content of between about 0.5 and about 6% by weight, and containing between about 0.003 and about 0.03% by weight of diethylene triamine penta(methylenephosphonic acid) or a physiologically compatable salt thereof, and compositions for use in such method.

10 Claims, No Drawings

METHOD OF DISINFECTING A SOFT CONTACT LENS WITH A DIETHYLENE TRIAMINE PENTA(METHYLENEPHOSPHONIC ACID) STABILIZED HYDROGEN PEROXIDE SOLUTION

This is a continuation of application Ser. No. 917,947 filed on Oct. 14, 1986, now abandoned.

BACKGROUND OF THE INVENTION

The present invention relates to an improved method of disinfecting a soft lens with a stabilized aqueous hydrogen peroxide solution having a hydrogen peroxide content from about 0.5 to about 6% by weight hydrogen peroxide wherein the stabilized solution contains from about 0.003 and about 0.03% by weight of diethylene triamine penta (methylenephosphonic acid) or a physiologically compatable salt thereof.

Soft contact lenses are characteristically prepared from hydrophilic polymers, such as polymers of hydroxyethyl methacrylate (HEMA), crosslinked with a conventional crosslinking agent, such as ethylene glycol dimethacrylate (EGDMA), or more complex copolymer systems including copolymers of HEMA, EGDMA, methacrylic acid and/or poly-N-vinylpyrrolidone, and the like. Other hydrophilic monomers conventionally employed in varying amounts in the manufacture of soft contact lenses include, for example, N-vinylpyrrolidone, glyceryl methacrylate, diethylene glycol monomethacrylate, triethylene glycol monomethacrylate, allyl 2-hydroxyethyl ether, acrylic acid, acrylamide, N,N-dimethylacrylamide, and the like. Other conventional crosslinking agents commonly employed include, inter alia, diallyl ether, divinyl benzene, diethylene glycol dimethacrylate, triethylene glycol dimethacrylate, diallyl succinate, allyl methacrylate, glycerin tri-methacrylate, and the like. Moreover, various amounts of relatively hydrophobic monomer units can be employed in the manufacture of soft contact lens materials, as long as the final copolymer network exhibits the desired hydrophilic characteristics. Typical hydrophobic monomers include methyl methacrylate, glycidyl methacrylate, N-(1,1-dimethyl-3-oxobutyl)acrylamide, siloxane methacrylates, perfluoroalkyl methacrylates, perfluoroalkoxyperfluoroalkyl methacrylates, and the like. In general, such lenses exhibit marked hydrophilic properties and, when wet, absorb water and are soft and flexible.

While these lenses are not actually perforate, they do have a sufficient degree of molecular porosity to permit water, oxygen and tear fluids to permeate the lens structure. In order for the disinfection of such lenses to be effective after they have been worn, it is important that contaminants be removed from both surfaces, and the interior of the lens, to the extent contaminants are present therein. Hydrogen peroxide in the form of a dilute solution, e.g. about 0.5 to 6% by weight in water, is known to be effective for use with contact lenses in order to kill any contaminating microorganisms.

One drawback with unstabilized dilute hydrogen peroxide solutions, however, is that without the use of a stabilizer or a combination of stabilizers, the aqueous peroxide solutions characteristically decompose over a period of time. The rate at which such dilute hydrogen peroxide solutions decompose will, of course, be dependent upon such factors as pH and the presence of trace amounts of various metal impurities, such as copper or chromium, which may act to catalytically decompose the same. Moreover, at moderately elevated temperatures the rate of decomposition of such dilute aqueous hydrogen peroxide solutions is greatly accelerated.

A large variety of stabilizers have been proposed for use with hydrogen peroxide to deactivate trace catalytic impurities, including stannous salts, ethylene diamine tetracetic acid, and the like.

For example, U.S. Pat. No. 3,860,391 discloses bleaching both compositions containing hydrogen peroxide and, as a stabilizer, amino lower alkylene polyphosphates, including diethylene triamine penta (methylenephosphinic acid) or salts thereof, and/or hydroxy alkane phosphates, with or without additional stabilizer constituents, and adjusted to a pH of between about 9.0 and 12.0 with, e.g. sodium hydroxide, for the bleaching of cellulose materials. Exemplified are compositions having a pH of 12.0.

Unfortunately, such highly basic compositions are undesirable in a contact lens environment and especially in th disinfection of contact lenses.

Thus, it is essential that the hydrogen peroxide containing solutions employed be, upon disinfection of the contact lenses and decompositon of the hydrogen peroxide, sufficiently compatable with the ocular environment so as not to occasion ocular irritation or damage if the disinfected contact lens containing the residual solution absorbed by the lens, is placed into the eye.

Caustic compositions, for example, can occasion severe ocular irritation and damage to the ocular tissue.

It is thus an object of the present invention to provide a method of disinfecting a soft contact lens with a stabilized aqueous hydrogen peroxide solution having a pH of about 5 to about 7, employing diethyene triamine penta (methylenephosphinic acid) or a physiologically compatable salt thereof, as a stabilizer, such that upon disinfection of such contact lens and decomposition of residual hydrogen peroxide, the resulting solution, absorbed by and adhering to said lens, is physiologically tolerable to the ocular environment.

It is a further object of the present invention to provide stabilized aqueous hydrogen peroxide solutions for use in such method.

These and other objects of the present invention are apparent from the following more specific disclosures.

DETAILED DESCRIPTION OF THE INVENTION

One embodiment of the present invention relates to a method of disinfecting a soft contact lens with a stabilized aqueous hydrogen peroxide solution having a pH between about 5.5 and about 7.5, a hydrogen peroxide content of between about 0.5 and about 6% by weight, and containing between about 0.003 and about 0.03% by weight of diethylene triamine penta(methylenephosphonic acid) or a physiologically compatable salt thereof, as a stabilizer, such that the solution, upon decomposition of the hydrogen peroxide, is physiologically tolerable to the ocular environment.

An alternate embodiment of the present invention relates to a stabilized aqueous hydrogen peroxide solution adapted for use in the disinfection of a soft contact lens, having a pH of between about 5.5 and about 7.5, a hydrogen peroxide content of between about 0.5 and about 6% by weight, and containing between about 0.003 and about 0.03% by weight of diethylene triamine penta(methylenephosphonic acid) or a physiologically compatable salt thereof as a stabilizer, wherein said solution, upon decomposition of the hydrogen peroxide, is physiologically tolerable to the ocular environment.

Physiologically compatable salts of diethylene triamine penta(methylenephosphonic acid) include, for example, water soluble salts with conventional pharmaceutically acceptable cationic moieties, including the alkali metal, alkaline earth metal, ammonium and amine cations. Suitable amine salts include, for example, mono-, di- and tri-lower alkyl amines, such as methylamine, ethylamine, diethylamine, triethylamine, dimethylamine, trimethylamine, propylamine, and the like; and mono-, di- and tri- lower hydroxyalkyl amines, such as ethanolamine, diethanolamine, triethanolamine, glucamine, 2-hydroxypropylamine, and the like.

By "lower" in the context of an alkyl group is meant up to 6 carbon atoms, preferably up to 4 carbon atoms.

Preferably, the concentration of hydrogen peroxide in the stabilized solution is between about 2% and 6% by weight, based upon the weight of the formulation.

Preferably, the concentration of diethylene triamine penta(methylenephosphonic acid) or salt thereof is present in the stabilized composition in an amount between about 0.006 and about 0.02% by weight of the composition, and most preferably between about 0.006 and about 0.0120% by weight of the composition.

If desired, additional conventional stabilizers may be employed in conjunction with the diethylene triamine penta(methylenephosphonic acid) or salt stabilizer in accordance with the present invention.

Suitable conventional stabilizers include: water soluble stannates, such as an alkali metal or ammonium stannates, for example sodium stannate, alone or in combination with a water soluble phosphate, polyphosphate or metaphosphate salt, such as an alkali metal or ammonium salt thereof; or an amino polycarboylic acid chelating agent, such as ethylene diamine tetraacetic acid, nitrilo triacetic acid or a water soluble salt thereof, such as an alkali metal or ammonium salt, especially the sodium salt, or mixtures thereof. Where such additional stabilizers are employed, they are general employed in a physiologically tolerable amount, e.g. in an amount of about 0.002 to about 0.1% by weight.

The pH of the stabilized solution is, as stated above, between about 5.5 and about 7.5. Preferably, the pH of the stabilized hydrogen peroxide solution is between about 6 and about 7, most preferably between about 6.2 and about 6.8. The pH can be adjusted as desired by incorporation of suitable amounts of acid or base of a physiologically tolerable nature in the amounts employed.

Also, there may be present in the stabilized hydrogen peroxide solution according to the present invention, one or more conventional, substantially inert, physiologically acceptable tonicity enhancing agents. Suitable such agents include, for example alkali metal halides, phosphates, hydrogen phosphates, and borates. Preferred are sodium chloride, sodium phosphate monobasic and sodium phosphate dibasic. The function of such tonicity enhancing agents is to increase the comfort level of the solution, upon decomposition of the hydrogen peroxide during or subsequent to contact lens disinfection, which adheres to the contact lens, in the eye of the patient.

Preferably sufficient tonicity enhancing agents are present in the solution, such that, upon decomposition of the hydrogen peroxide therein, the resulting solution is substantially isotonic, e.g. substantially equivalent to a 0.9% by weight aqueous sodium chloride solution.

In use, the contact lens to be disinfected is removed from the eye of the patient and placed into a solution of the stabilized hydrogen peroxide to disinfect the lens. Upon disinfection the hydrogen peroxide is decomposed, e.g. by the use of a conventional catalyst, such as a platinum catalyst on a support, or catalase, or by the use of a physiologically acceptable hydrogen peroxide decompositon agent, such as a physiologically acceptable reducing agent, including pyruvic acid or suitable salts thereof, e.g. the sodium salt. The lens can thereafter be stored in the resulting solution until reinsertion into the eye.

In general, the stabilized hydrogen peroxide solutions of the present invention are characterized by their extraordinary stability, even under accelerated conditions, for example by heating the solutions to 100° C for 24 hours. Moreover, the instant compositions are characterized by their physiological tolerability subsequent to hydrogen peroxide decomposition.

The following examples are presented for illustrative purposes and are not intended to limit the scope of this invention. All parts are by weight unless otherwise indicated.

EXAMPLE 1

Into 80 ml distilled deionized water there is added 0.8655 g sodium chloride, 0.0622g sodium phosphate dibasic (anhydrous), 0.0072g sodium phosphate monobasic (monohydrate) and 0.006g ethylene diamine penta(methylenephosphonic acid) with stirring. To the resulting solution there is added 31% aqueous hydrogen peroxide in an amount of 10 ml, and sufficient distilled deionized water is added to result in a total volume of 100 ml. Thereupon the pH is adjusted to 6.5 by the addition dropwise of dilute aqueous HCl or NaOH.

The resulting stabilized 3% hydrogen peroxide is then heated to 100° C for a period of 24 hours. The solution possessed a "hot stability" of above 95%, i.e. the ratio of the hydrogen peroxide present in the after-heated sample to the before-heated sample, multiplied by 100%, exceeded 95%.

EXAMPLE 2

The procedure of Example 1 was duplicated, except that typical deionized water is employed. Again, the hot stability of the resulting stabilized hydrogen peroxide solution is above 95%.

EXAMPLE 3

The procedure of Example 1 was duplicated, except that conventional soft tap water is employed. Once again, the hot stability of the resulting stabilized hydrogen peroxide solution is above 95%.

What is claimed is:

1. A method of disinfecting a soft contact lens comprising contacting said lens with a stabilized aqueous hydrogen peroxide solution having a pH between about 5.5 and about 7.5, a hydrogen peroxide content of between about 0.5 and about 6% by weight, and containing between about 0.003 and about 0.03% by weight of diethylene triamine penta(methylenephosphonic acid) or a physiologically compatable salt thereof, as a stabilizer, such that the solution, upon decomposition of the hydrogen peroxide, is physiologically tolerable to the ocular environment.

2. A method according to claim 1, wherein said solution has a hydrogen peroxide content of about 2 to about 6% by weight, based upon the weight of solution.

3. A method according to claim 1, wherein the pH is between about 6 and about 7.

4. A method according to claim 1, wherein the pH is between about 6.2 and about 6.8.

5. A method according to claim 1, in which the concentration of diethylene triamine penta(methylenephosphonic acid) is between about 0.006 and about 0.02% by weight of the composition.

6. A method according to claim 1, wherein said solution, upon decomposition of the hydrogen peroxide therein, is substantially isotonic.

7. A method according to claim 2, wherein said solution, upon decomposition of the hydrogen peroxide therein, is substantially isotonic.

8. A method according to claim 1, wherein, upon disinfection of said lens, the hydrogen peroxide in said solution is decomposed by the use of an effective amount of a hydrogen peroxide decomposition catalyst or agent.

9. A method according to claim 8, wherein upon hydrogen peroxide decomposition, said solution is substantially isotonic.

10. A method according to claim 1, in which said solution additionally contains between about 0.002 and 0.1% of a water soluble stannate or amino polycarboxylic acid chelating agent.

* * * * *